United States Patent [19]

Frampton et al.

[11] 4,354,978

[45] Oct. 19, 1982

[54] PROCESS FOR PREPARING ALPHA-METHYL MONOBASIC ACID AND ESTERS THEREOF

[75] Inventors: Orville D. Frampton, Wyoming; William D. Baugh, Cincinnati, both of Ohio

[73] Assignee: National Distillers & Chemical Corp., New York, N.Y.

[21] Appl. No.: 174,954

[22] Filed: Aug. 4, 1980

[51] Int. Cl.³ .......................... C11C 3/02; C11C 1/00
[52] U.S. Cl. ............................ 260/410.9 R; 260/413; 560/233; 562/522
[58] Field of Search ................ 260/410.9 C, 413 HC, 260/410; 560/114, 207, 233; 562/406, 497, 522

[56] References Cited

U.S. PATENT DOCUMENTS 3,437,676  4/1969  Von Kutepow ................... 560/233
3,641,074  2/1972  Fenton ........................ 260/410.9 C
3,700,706 10/1972  Butter ............................ 560/114
3,780,074 12/1973  Romanelli .................... 260/410.9 C
3,887,595  6/1975  Nozaki .............................. 260/413

*Primary Examiner*—John F. Niebling
*Attorney, Agent, or Firm*—Kenneth D. Tremain

[57] ABSTRACT

Alkanoic acids containing largely the alpha-methyl isomers thereof, and/or the corresponding esters, are prepared by reacting an alpha-olefin, carbon monoxide and water and/or a monoalkanol in the presence of a catalytically effective amount of a catalyst composition comprising (i) a zero-valent Group VIII metal or metal alloy in which the Group VIII metal is the major component by weight thereof, (ii) an aryl ligand selected from the group consisting of arylarsine, arylstibine and arylbismuthine and (iii) a Lewis acid and/or hydrochloric acid.

13 Claims, No Drawings

PROCESS FOR PREPARING ALPHA-METHYL MONOBASIC ACID AND ESTERS THEREOF

BACKGROUND OF THE INVENTION

1. Field of the Invention

The present invention relates to the field of processes for the preparation of alkanoic acids and alkanoic acid esters and, more particularly, to the preparation of such acids and esters from the catalyzed reaction of olefin, carbon monoxide and water and/or alkanol (a type of carbonylation reaction).

2. Description of the Prior Art

It is known from U.S. Pat. No. 3,952,034 to react an olefin or acetylene, carbon monoxide and water or alkanol in the presence of a soluble, i.e., homogeneous, catalyst system containing a polynuclear complex of palladium and iron or metal of Groups IVA, VA or IIIB, or a mixture of a soluble palladium salt and metal halide, to provide a carboxylic acid or ester. A similar reaction is described in German Patent No. 27 39 096 which also employs a soluble palladium compound or complex in combination with an aryl arsine as catalyst. Still other soluble palladium-containing catalysts for the aforedescribed carbonylation reaction are disclosed in U.S. Pat. Nos. 3,641,074; 3,816,490; 3,859;319; 3,919,272; 3,892,788; 3,917,677; 3,965,132; 3,968,133; and 3,987,089. While U.S. Pat. No. 3,887,595 describes the use of zero-valent palladium metal as a component of the carbonylation catalyst system, the result of the reaction is to provide a high ratio of straight-chain to branch-chain carboxylic acids and esters. For some important industrial applications, for example, monomer precursors or lubricants, it is highly desirable to provide a reaction product which is exclusively made up of branched product or a product in which the branched product at least predominates. Although some of the fully soluble catalyst systems heretofore known in the carbonylation of alkenes and alkynes may be effective for providing relatively high ratios of branched carboxylic acids and esters in relation to the quantities of straight-chain product produced, nevertheless they are at an operational disadvantage compared to the insoluble, i.e., heterogenous, catalyst systems since the solubility of the former complicates product separation and recovery procedures.

Accordingly, there has heretofore existed a need for an effective heterogenous catalyst system for the reaction of olefin, carbon monoxide and water and/or alkanol to provide predominantly alpha-methyl monoalkanoic acid and/or ester.

SUMMARY OF THE INVENTION

It has now been discovered that alpha-olefin of from 3 to 8 carbon atoms, carbon monoxide and water and/or monoalkanol can be reacted to provide predominantly alpha-methyl monoalkanoic acids of from 4 to 9 carbon atoms and/or the esters thereof by employing as catalyst, a catalytically effective amount of (i) at least one zero-valent Group VIII metal and/or metal alloy, (ii) at least one aryl ligand selected from the group consisting of arylarsine, arylstibine and arylbismuthine and (iii) a Lewis acid and/or hydrochloric acid.

Use of the foregoing catalyst system which is heterogeneous in its Group VIII metal or metal alloy component greatly facilitates separation of such component from the liquid reaction product(s) leading to an overall simplification of the carbonylation process.

DESCRIPTION OF THE PREFERRED EMBODIMENTS

The alpha-olefins which are useful in the process of this invention contain from 3 to 8 carbon atoms and include propylene, 1-butene, 1-pentene, 1-hexene, 1-heptene, 1-octene, 3-methyl-1-pentene, 4-methyl-1-pentene, 4,4-dimethyl-1-pentene, and the like.

When the desired carbonylation product is to be a branched carboxylic acid, water is employed as a reactant. The use of a monoalkanol reactant under the same conditions will provide a branched carboxylic acid monoester and aqueous monoalkanol will, of course, provide a mixture of acid and ester. The preferred monoalkanols are the monoalkanols of from 1 to 20 carbon atoms such as methanol, ethanol, propanol, butanol, isobutanol, decanol, dodecanol, and the like.

The catalyst composition of the present invention comprises, as a first component, at least one zero-valent Group VIII metal which can be ruthenium, rhodium, palladium, osmium, iridium or platinum, alone or alloyed with one or more other Group VIII metals and/or minor amounts by weight of one or more other metals such as iron, cobalt, copper, gold, etc. Palladium metal is preferred for its high catalytic activity. It is further preferred to employ the metal and/or metal alloy in supported form, i.e., applied to an inert particulate carrier such as silica, silica xerogel, alumina, titania, zirconia, carbon, diatomaceous earth, etc., as is widely practiced in the art.

The second component of the catalyst compositions of this invention is an aryl ligand selected from the arylarsines, arylstibines and arylbismuthines in which the aryl moiety can be chosen from such unsubstituted and substituted aromatic groups as phenyl, tolyl, xylyl, para-ethylphenyl, para-tertbutylphenyl, m-octylphenyl, 2,4-diethylphenyl, para phenylphenyl, meta-benzylphenyl, 2,4,6-trimethylphenyl, para-methoxyphenyl, meta-chlorophenyl, meta-trifluoromethylphenyl, para-propoxyphenyl, para-carbethoxyphenyl, and so forth. Triphenylarsine provides particularly good results and as it is readily commercially available, is preferred for use herein.

The third component of the instant catalyst compositions is an acid which may be a Lewis acid such as aluminum chloride which is preferred, ferric chloride or chromic chloride and/or the Bronsted acid hydrochloric acid.

The quantities of zero-valent Group VIII metal employed in the catalyst compositions herein can vary over wide limits, for example, from about 0.00001 to about 1.0 mole percent of such metal per mole of alpha-olefin provides entirely acceptable results with from 0.0001 to about 0.1 mole percent being preferred. Similarly, the amounts of aryl ligand (provided it is in large molar excess compared to Group VIII metal) and Lewis acid and/or hydrochloric acid can also vary widely. Thus, a molar ratio of aryl ligand to Group VIII metal of from about 5:1 to about 100:1, and preferably from about 10:1 to about 20:1, and a molar ratio of Lewis acid and/or hydrochloric acid to Group VIII metal of from about 1:1 to about 30:1, and preferably from about 1:1 to about 20:1, generally provides good results.

The reaction of alpha-olefin, carbon monoxide, water and/or monoalkanol can be carried out batch-wise with agitation in an autoclave or similar pressure vessel or continuously in a tubular reactor. Although carbonylation consumes one mole of carbon monoxide for each mole of alpha-olefin, it is preferred to employ an excess of carbon monoxide relative to olefin, e.g., from about 2:1 to about 100:1 excess. Similarly, while the carbonylation reaction consumes one mole of water or monoalkanol per mole of olefin, it is also preferred to use a large excess of this reactant compared to olefin, e.g., from about 2:1 to about 20:1, to insure an efficient reaction. Operating temperatures and pressures are not critical and can be selected from over a wide range. Thus, temperatures on the order of from about 50° C. to about 300° C., and preferably from about 100° C. to about 200° C., are entirely satisfactory. Partial pressures of carbon monoxide of from about 300 psig to about 3,000 psig, preferably from about 500 psig to 2,000 psig, generally provides good results. The time of the reaction can vary from a few minutes to twelve hours or more with substantial conversions of alpha-olefin usually being achieved within 2 to 8 hours. While the use of a solvent is not required, it may be convenient or desirable to employ a liquid solvent or diluent which is inert under the reaction conditions such as the saturated or aromatic hydrocarbons, for example, pentane, cyclohexane, gasoline hydrocarbons, benzene, toluene, and the like, ketones, amides, ethers, esters, and so forth. Whenever a solvent is employed, the amount is not critical and can therefore vary widely. Amounts of solvent of from about 10% to about 500% by weight of the total reactants are usually satisfactory.

Recovery of the carboxylic acids and/or ester products can be accomplished by known and conventional means such as distillation, solvent extraction, and the like.

EXAMPLE 1

The following charge, designated Charge A, was placed in a 71 ml Parr Hastelloy C reactor: 16.6 ml (0.41 moles) methanol, 0.681 g (0.0187 moles) anhydrous HCl, 5 g (0.119 moles) propylene and 0.620 g (0.00203 moles) triphenylarsine. The catalyst charge was 0.5 g 5% palladium metal dispersed on carbon powder ($2.35 \times 10^{-4}$ g atom $Pd^0$). The following procedure, designated Procedure B, was used to charge CO, carry out the reaction, and work up the reaction mixture: The reactor cover, having a valved port at its top was placed on the reactor and fastened. Carbon monoxide at 3000 psig and ambient temperature (about 25° C.) was introduced into the vessel through the valve, after which the valve was closed, the reactor placed in a shaker in a heated constant temperature oven at 100° C. and shaken six hours. After reaction, the reactor was cooled to ambient temperature, vented, then opened. The clear liquid was separated from the solid catalyst by decantation. Gas chromatographic analysis showed combined selectivity of methyl isobutyrate and methyl butyrate to be 98.4% and the mole ratio of methyl isobutyrate to methyl n-butyrate to be 5.56. Substantial yields of these esters were obtained.

EXAMPLE 2

A 71 ml Parr Hastelloy C reactor was charged with 0.614 g of the solid catalyst residue from Example 1 and charge A. After employing Procedure B, the liquid reaction mixture was analyzed as in Example 1. Substantial concentrations of methyl isobutyrate and methyl n-butyrate in a ratio of branched to straight chain esters of 5.7:1 were found. The selectivity of butyrate esters was 99.3%.

EXAMPLE 3

A 71 ml Parr Hastelloy C reactor was charged with 0.573 g of the solid catalyst residue recovered from Example 2 and Charge A. After employing Procedure B, the liquid reaction mixture was analyzed as in Example 1. Substantial concentrations of methyl isobutyrate and methyl n-butyrate in a ratio of branched to straight chain esters of 4.1:1 were found. The selectivity of butyrate esters was 98.7%.

EXAMPLE 4

The importance of using high mole ratios of aryl ligand compared to Group VIII metal (such as the 8.7 ratio used in Charge A) is demonstrated in this example by omitting added triphenylarsine from the charge and employing only that amount of triphenylarsine present in the previously recovered catalyst.

A 71 ml Parr Hastelloy C reactor was charged with the solid catalyst residue from Example 3, and Charge A (omitting added triphenylarsine from the charge). After employing Procedure B and analyzing the liquid product, it was found that although some methyl isobutyrate and methyl n-butyrate were formed in a ratio of branched to unbranched esters of 4.3, the yield of esters was much lower than in any of the previous examples, amounting to only 7.6% of that formed in Example 3. The selectivity to butyrate esters was 94.5%.

EXAMPLE 5

Charge B, which is equivalent to Charge A except that 0.43 g (0.0032 moles) of $AlCl_3$ were used instead of 0.681 g (0.0177 moles) of anhydrous HCl, was placed in a 71 ml Parr Hastelloy C reactor together with 0.5 g 5% Pd metal dispersed on carbon powder ($2.35 \times 10^{-4}$ g atom $Pd^0$). Following Procedure B, the liquid product was found by chromatographic analysis to contain substantial concentrations of methyl isobutyrate and methyl n-butyrate in a ratio of branched to straight chain esters of 5.7 to 1, and a selectivity to butyrate ester of 99.1%.

EXAMPLE 6

A 71 ml Parr Hastelloy C reactor was charged with the solid catalyst residue from Example 5 and with Charge B. After following Procedure B, the liquid product was found by chromatographic analysis to contain substantial concentrations of methyl isobutyrate and methyl n-butyrate in a ratio of branched to straight chain esters of 4.3 to 1, and a selectivity to butyrate esters of 98.6%.

EXAMPLE 7

The following example shows that high mole ratios of triphenylarsine to Group VIII metal, e.g., at least about 5:1, are needed to obtain good yields of butyrate esters and high ratios of isobutyrate to n-butyrate esters.

A 71 ml Parr Hastelloy C reactor was charged with 0.5 g 5% palladium metal dispersed on carbon catalyst ($2.35 \times 10^{-4}$ g atoms Pd metal) and Charge A with the exception that the triphenylarsine product was omitted. Following Procedure B, the liquid product was analyzed by gas chromatography. The yield of butyrate esters was very low, amounting to only 12.6% of that obtained in Example 1 where triphenylarsine was included. The mole ratio of branched to straight chain esters was only 2.8 and selectivity of butyrate esters was 95.5%.

EXAMPLE 8

A 71 ml Parr Hastelloy C reactor was charged with 2 g of a palladium-gold alloy on silica carrier ⅛" extrudate containing 1.3% Pd metal and 0.6% gold metal corresponding to $2.44 \times 10^{-4}$ g atoms palladium, and Charge C which is equivalent to Charge A except that 0.8 g anhydrous HCl was used instead of 0.681 g. Following Procedure B, the liquid product was analyzed and found to contain substantial concentrations of methyl isobutyrate and methyl n-butyrate with a mole ratio of branched chain ester to straight chain ester of 8.3. The selectivity of butyrate esters was 99.7%.

EXAMPLE 9

A 71 ml Hastelloy C Parr reactor was charged with the solid catalyst recovered from Example 8 and Charge C. After employing Procedure B, the liquid product was found to contain substantial concentrations of methyl butyrate esters with selectivity to butyrate esters of 99.9% and a mole ratio of methyl isobutyrate to methyl n-butyrate of 5.6 to 1.0.

EXAMPLE 10

A 71 ml Hastelloy C Parr reactor was charged with Charge C and a palladium metal catalyst consisting of 0.5 g of 5% Pd metal on ground alumina. After employing Procedure B, the liquid product was found to contain substantial concentrations of butyrate esters with selectivity of 99.4% and a mole ratio of methyl isobutyrate to methyl n-butyrate of 10.7 to 1.

EXAMPLE 11

A 71 ml Hastelloy C Parr reactor was charged with the solid catalyst from Example 10 and Charge C. After employing Procedure B, the liquid product was found to contain substantial concentrations of methyl butyrate esters with a selectivity of 99.6% and a mole ratio of methyl isobutyrate to methyl n-butyrate of 6.7 to 1.

EXAMPLE 12

A 71 ml Hastelloy C Parr reactor was charged with the solid catalyst from Example 11 and Charge C. After employing Procedure B, the liquid product was found to contain substantial concentrations of methyl butyrate esters with a selectivity of 99.7% and a mole ratio of methyl isobutyrate to methyl n-butyrate of 9.49 to 1.

EXAMPLE 13

A 71 ml Parr Hastelloy C reactor was charged with 1.0 g of 2% Pd metal dispersed on alpha-alumina pellets and Charge C. After employing Procedure B, the liquid product was found to contain substantial concentrations of methyl butyrate esters with a selectivity of 96.2% and a mole ratio of methyl isobutyrate to methyl n-butyrate of 6.3.

EXAMPLE 14

A 71 ml Parr Hastelloy C reactor was charged with the solid catalyst residue from Example 13 and Charge C. After employing Procedure B, the liquid product was found to contain substantial concentrations of methyl butyrate esters with a selectivity of 99.5% and a mole ratio of methyl isobutyrate to methyl n-butyrate of 7.7.

EXAMPLE 15

A 71 ml Parr Hastelloy C reactor was charged with the solid catalyst residue from Example 14 and Charge C. After employing Procedure B, the liquid product was found to contain substantial concentrations of methyl butyrate esters with a selectivity of 99.3% and a mole ratio of methyl isobutyrate to methyl n-butyrate of 6.2.

EXAMPLE 16

One of two 71 ml Parr Hastelloy C reactors (reactor X) was charged with Charge C, and 0.5 g of 5% Pd metal on alpha-alumina. The other reactor (reactor Y) was also charged with Charge C except that the 0.620 g of triphenylarsine was omitted. Added also were 0.186 g of dichlorobistriphenylarsine palladium (II) prepared by adding a solution of triphenylarsine in ethanol to an acidified aqueous solution of palladium dichloride salt. The gram atoms of palladium ($2.35 \times 10^{-4}$ g atoms Pd) was equivalent in the two reactors. However, reactor Y contained only $4.71 \times 10^{-4}$ moles of triphenylarsine while reactor X contained $20.26 \times 10^{-4}$ moles. After following Procedure B, the liquid products from the two reactors were analyzed. The selectivity of methyl butyrate esters was 99.9% for reactor X and 99.1% for reactor Y. The mole ratio of methyl isobutyrate to methyl n-butyrate was 9.56 for reactor X and 5.39 for reactor Y. The area percent on the chromatogram for methyl isobutyrate and for methyl n-butyrate were 39.98% and 4.18% for reactor X but only 7.45% and 1.38% for reactor Y showing a much higher yield was obtained in reactor X than in reactor Y.

EXAMPLE 17

In this example, the product esters are distilled from the catalyst system (the residue) comprising supported palladium metal and triphenyl arsine, and the catalyst system reused.

A 71 ml Hastelloy C Parr reactor was charged with Charge D consisting of 5 g propylene, 16.6 ml of methanol containing 0.8 g HCL, 0.620 g triphenyl arsine and 0.5 g of 5% Pd metal on ground alpha-alumina. Procedure B was followed up to the point where the reactor was opened. At this point the reactor contents were analyzed by gas-liquid chromatography, then transferred to a rotoevaporator and the methyl butyrates, methanol and HCl removed by distillation. The residue including the palladium and triphenylarsine were returned to the reactor for reuse. The chromatographic analysis showed substantial concentrations of methyl butyrates to be present with 99.9% selectivity and a ratio of methyl isobutyrate to methyl n-butyrate of 5.9.

The reactor containing the supported Pd metal and triphenylarsine portion of the used catalyst system was recharged with 5 g. propylene and 16.6 ml. methanol containing 0.8 g HCL and Procedure B again followed up to the point where the reactor was opened. The reactor contents were analyzed by gas-liquid chromatography, then transferred to the roto-evaporator and product esters, methanol and HCl removed by distillation after which the residue comprising a catalyst system (including palladium metal and triphenylarsine) was transferred to the reactor for a further reuse. Analysis of the reaction mixture showed substantial concentrations of methyl butyrates to be present with a selectivity of 99.8% and a mole ratio of methyl isobutyrate to methyl n-butyrate of 8.9.

In a third use of the catalyst system carried out in the same manner as outlined above, the gas-liquid chromotographic analysis also showed substantial concentrations of methyl butyrate to be present with selectivity of 99.6% and mole ratio of methyl isobutyrate to methyl n-butyrate of 7.0. There were no significant losses of palladium or triphenylarsine in the above operations.

EXAMPLE 18

This example shows that by including methyl n-butyrate in the charge, an improvement can be effected in the mole ratio of methyl isobutyrate to methyl n-butyrate synthesized from propylene, methanol, and carbon monoxide using a supported Pd metal and triphenylarsine as catalyst.

A 71 ml Hastelloy C Parr reactor was charged with 5 g. propylene, 13.6 ml methanol containing 0.8 g HCl, 3.0 ml methyl n-butyrate ($26.4 \times 10^{-3}$ moles), 0.620 g triphenylarsine and 0.5 g of 5% Pd on ground alpha-alumina.

After following Procedure B, analysis of the liquid product showed substantial concentrations of methyl butyrates to be present with a selectivity of 99.9% with a calculated mole ratio of synthesized methyl isobutyrate to methyl n-butyrate of 16.4 to 1. The calculation took into account an analysis prior to carbonylation and a volume increase after carbonylation.

EXAMPLE 19

A 71 ml Hastelloy C Parr reactor was charged with 5 ml ($319 \times 10^{-4}$ moles) octene-1, 0.4 g AlCl$_3$, 15 ml (0.371 moles) methanol, 0.620 g ($20.3 \times 10^{-4}$ moles) triphenylarsine and 2.0 g 1.3% Pd/0.6% Au alloy on silica (corresponding to $2.44 \times 10^{-4}$ g atom of Pd). The reactor was closed, pressurized to 3000 psi at ambient temperature with CO, and heated to 1000° C. and shaken six hours. The final pressure at 100° C. was 3,900 psig.

After reaction, the reactor was cooled, opened and liquid contents analyzed. The analysis showed substantial concentrations of methyl 2-methyloctanoate and methyl n-nonanoate in a mole ratio of branched to unbranched ester of 2.5 to 1. The conversion was 51% and selectivity to the above esters was above 99%.

EXAMPLE 20

A stirred pressure vessel at 3,000 psig partial CO pressure and at 100° C. is charged continuously at a selected rate with a slurry from a feed mixing tank containing aluminum chloride, methanol, triphenylarsine, methyl n-butyrate and a solid catalyst powder comprising 5% palladium metal on ground alpha-alumina in corresponding mole ratios of 0.32:41:0.203:1.4:0.0234, respectively. Propylene is also charged to the vessel from a propylene storage tank at a mole ratio to methanol of 11.9:41. CO is added continuously on demand to maintain the pressure 3,000 psig.

Part of the liquid reaction slurry is continuously removed from the vessel through a valve into a flash drum at a rate approximating the feed rate but maintaining the reaction volume constant. Pressure is let down to atmospheric in the flash drum and dissolved gases are flashed off. These gases are comprised principally of unreacted propylene and carbon monoxide and are led to a compressor where they are continuously recompressed to 3,000 psig and recycled to the reactor.

The liquid reaction slurry is led to a centrifuge where solid catalyst residues are separated continuously and sent to a stirred catalyst slurry tank. The supernatant liquid reaction mixture is fed continuously to a continuous methanol still.

Methanol is separated as overhead in the still and sent to methanol storage. The still bottoms are pumped to a continuous methyl isobutyrate still where methyl isobutyrate is separated as overhead and sent to methyl isobutyrate product storage. These still bottoms are then pumped to a continuous methyl n-butyrate still where methyl n-butyrate corresponding to the amount synthesized is sent to methyl n-butyrate storage, the remainder is recycled with the still bottoms (after removing a small purge) to the stirred catalyst slurry tank from which, together with solid catalyst residues, it is sent to the feed mixing tank.

The feed mixing tank is initially charged with aluminum chloride, methanol, catalyst and triphenylarsine in the ratios set forth above. Under steady state conditions, however, only make-up quantities of these reagents need be added to replace material removed from the system by the purge and by-product separation.

EXAMPLE 21

Example 5 was repeated except that 3.56 g (0.039 moles) FeCl$_3$ were used instead of 0.43 g (0.0032 moles) AlCl$_3$. Following Procedure B, the liquid product contained methyl isobutyrate and methyl n-butyrate in a mole ratio of branched to straight chain esters of 5 to 1.

EXAMPLE 22

Example 7 was repeated except that 3.0 g (0.0343 moles) CrCl$_3$ was used instead of the 3.56 g (0.039 moles) FeCl$_3$. Following Procedure B, the liquid product contained methyl isobutyrate and methyl n-butyrate in a mole ratio of 4.2 to 1.

EXAMPLE 23

A fixed bed tubular reactor at 100° C. and at 3,000 psig partial pressure CO and containing a solid catalyst of 5% palladium metal on an alpha-alumina support having a particle size in terms of the Martin diameter in the range of from 2 to 15 millimeters is continuously charged at the top with a liquid reaction mixture from a feed mixing tank containing methanol, HCl, methyl n-butyrate and tri-phenylarsine maintained at 100° C. in corresponding mole ratios of 41:2.2:1.4:0.203, with propylene in a ratio to methanol of 11.9 to 41, and with carbon monoxide to bring the pressure to 3,000 psig. From this point on, CO is added on demand to maintain a 3,000 psig pressure.

Effluent liquid and gas from the bottom of the catalyst bed is removed continuously through a valve where pressure is let down to atmospheric. The effluent is passed into a flash drum where gas including dissolved gas comprised of unreacted propylene and carbon monoxide is separated and led to a compressor where it is compressed to 3,000 psig, then recycled to the reactor.

The liquid product is fed continuously to a methanol still where methanol is separated as overhead and pumped to methanol storage for subsequent use in making up the feed in the feed mixing tank.

Bottoms from the methanol still are pumped to a continuous methyl isobutyrate still where methyl isobutyrate is separated and pumped to methyl isobutyrate product storage. Bottoms from the methyl isobutyrate still are pumped to a methyl n-butyrate still and methyl n-butyrate corresponding to that synthesized is separated and pumped to methyl n-butyrate storage. The bottoms comprising triphenylarsine and residual methyl n-butyrate are pumped to the feed mixing tank.

The composition of the feed mixing tank is kept constant by addition of feed ingredients as needed.

What is claimed is:

1. A process for preparing alpha-methyl monoalkanoic acid of from 4 to 9 carbon atoms, and/or the monoester thereof, wherein said branched acid and/or ester predominates over any unbranched acid and/or ester which may also be produced, which comprises reacting an alpha- monoolefin of from 3 to 8 carbon atoms, carbon monoxide and water and/or monoalkanol in the presence of a catalytically effective amount of a heterogeneous catalyst composition comprising (i) a zero-valent Group VIII metal or metal alloy in which the Group VIII metal is the major component by weight thereof, (ii) an aryl ligand selected from the group consisting of arylarsine, arylstibine and arylbismuthine and (iii) a Lewis acid and/or hydrochloric acid to provide a liquid reaction product containing said monoalkanoic acid and/or monoester thereof.

2. The process of claim 1 wherein the alpha-olefin is selected from the group consisting of propylene, 1-butene, 1-pentene, 1-hexene, 1-heptene, 1-octene, 3-methyl-1-pentene, 4-methyl-1-pentene, and 4,4-dimethyl-1-pentene.

3. The process of claim 1 wherein the monoalkanol is selected from the group consisting of methanol, ethanol, propanol, butanol, isobutanol, decanol and dodecanol.

4. The process of claim 1 wherein the Group VIII metal is palladium.

5. The process of claim 1 wherein the Group VIII metal is supported on an inert particulate carrier.

6. The process of claim 1 wherein the aryl ligand is triphenylarsine.

7. The process of claim 1 wherein the Lewis acid is aluminum chloride.

8. The process of claim 1 wherein the reaction is carried out in an inert solvent or diluent.

9. The process of claim 1 wherein the reaction is carried out within a range of temperature of from about 50° C. to about 300° C.

10. The process of claim 1 wherein the reaction is carried out at a partial pressure of carbon monoxide of from about 300 psig to about 3,000 psig.

11. The process of claim 1 wherein carbon monoxide is used in large molar excess compared to alpha-olefin.

12. The process of claim 1 wherein water or monoalkanol is used in large molar excess compared to alpha-olefin.

13. The process of claim 1 wherein aryl ligand is used in large molar excess compared to Group VIII metal.

* * * * *